US011707736B2

(12) United States Patent
McGuire

(10) Patent No.: US 11,707,736 B2
(45) Date of Patent: Jul. 25, 2023

(54) MICROFLUIDIC CHIP AND METHOD FOR MAKING THE SAME

(71) Applicant: eNuvio Inc., Montreal (CA)

(72) Inventor: Hugo McGuire, Montreal (CA)

(73) Assignee: eNuvio Inc., Montreal (CA)

( * ) Notice: Subject to any disclaimer, the term of this patent is extended or adjusted under 35 U.S.C. 154(b) by 274 days.

(21) Appl. No.: 16/766,536

(22) PCT Filed: Dec. 7, 2018

(86) PCT No.: PCT/CA2018/051566
§ 371 (c)(1),
(2) Date: May 22, 2020

(87) PCT Pub. No.: WO2019/109190
PCT Pub. Date: Jun. 13, 2019

(65) Prior Publication Data
US 2021/0138459 A1     May 13, 2021

Related U.S. Application Data

(60) Provisional application No. 62/596,552, filed on Dec. 8, 2017.

(51) Int. Cl.
*B01L 3/00*      (2006.01)
*C12M 3/06*      (2006.01)
(Continued)

(52) U.S. Cl.
CPC ....... *B01L 3/502707* (2013.01); *C12M 23/16* (2013.01); *G01N 27/406* (2013.01); *G01N 33/48728* (2013.01); *G03F 7/0037* (2013.01); *G03F 7/2014* (2013.01); *B01L 2200/0689* (2013.01); *B01L 2300/0645* (2013.01); *B01L 2300/0832* (2013.01); *B01L 2300/0887* (2013.01); *B01L 2300/12* (2013.01)

(58) Field of Classification Search
None
See application file for complete search history.

(56) References Cited

U.S. PATENT DOCUMENTS

2012/0247980 A1* 10/2012 Burke ............... G01N 33/4833
                                                        205/792
2014/0342394 A1* 11/2014 Parker ............... G01N 33/5088
                                                        435/402

* cited by examiner

*Primary Examiner* — Lore R Jarrett
(74) *Attorney, Agent, or Firm* — Benoit & Côté Inc.; France Côté

(57) ABSTRACT

There is a described a patch-clamp chip for making electrical measurements on a biological sample. The patch-clamp chip comprising a plurality of layers comprising polydimethylsiloxane (PDMS) forming a stack. It comprises at least a chip surface layer comprising an aperture formed therethrough and which upwardly opens on the surface, where the biological sample is provided. A microfluidic channel layer comprising PDMS extends below the plane of the chip surface layer and comprises a microfluidic channel formed therein. The aperture of the chip surface layer downwardly opens on the microfluidic channel. Electrophysiological measurements are made between an internal solution in the microfluidic channel and the external solution on the chip surface. The measurements can be performed via a bottom electrode. A plurality of apertures and corresponding microfluidic channels can be provided to perform simultaneous measurements on a plurality of samples, independently.

5 Claims, 11 Drawing Sheets

(51) Int. Cl.
*G01N 27/406* (2006.01)
*G01N 33/487* (2006.01)
*G03F 7/00* (2006.01)
*G03F 7/20* (2006.01)

MICROFLUIDIC CHIP AND METHOD FOR MAKING THE SAME

CROSS-REFERENCE TO RELATED APPLICATIONS

This application claims priority from or benefit of U.S. provisional patent application 62/596,552, filed Dec. 8, 2017, the specification of which is hereby incorporated herein by reference in its entirety.

BACKGROUND

(a) Field

The subject matter disclosed generally relates to microfluidic chips. More specifically, it relates to a microfluidic chip for making measurements on cells and lipid bilayers, and to a method for making the microfluidic chip.

(b) Related Prior Art

The classic method of patch-clamp involves isolating a portion of a cell membrane using an electrolyte-filled glass micropipette. This enables the measurement of ionic current flowing through the isolated portion of the cell membrane via a class of membrane-bound protein called ion channels. These proteins are of utmost importance in physiology and are also major drug targets. Due to its extremely high sensitivity, patch-clamp electrophysiology is considered the "gold-standard" to assess the function of ion channels as well as their response to pharmaceutical compounds. This technique can provide key information in terms of kinetic behavior of ion channels, their selectivity, their type (or subtype) and their regulatory mechanisms. This rich information content is essential to study ion channels from a biophysical standpoint, but also to develop and test treatments or therapies to various pathologies.

To perform a conventional patch-clamp recording, the micropipette is brought in proximity to a cell using micromanipulators and a microscope. A seal between the cell and the micropipette tip, usually having a diameter on the order of about one micron, is formed by bringing the micropipette tip in contact with the cell membrane, generally with slight suction. Once in place, it is possible to obtain a seal, characterized electrically as a giga-Ohm seal (i.e., with an electrical resistance greater than 1 GOhm), between the micropipette and the cell membrane. By including Ag/AgCl electrodes within the micropipette as well as in the extracellular bathing solution, electrophysiological experiments can be performed in various configurations, as for example the so-called cell-attached, whole-cell and excised patch (inside-out and outside-out) configurations, by carefully adjusting the suction and the position of the micromanipulator. Alternatively, electrical pulses can be used to go from cell-attached to whole-cell mode by provoking the breakdown of the membrane at the micropipette tip. Despite its versatility and its capability to acquire high-resolution electrophysiological data, conventional patch-clamp also has several important drawbacks. In order to achieve an adequate seal and to generate good quality data in any of these configurations, the entire procedure requires highly-trained and experienced operators, and a high level of dexterity. The whole procedure can fail if any of the steps of the procedure is not performed perfectly. This technique also suffers from low throughput data output because of the overall difficulty of the process, as well as the steps requiring slow, highly precise movement of the micromanipulators. Moreover, complex and costly equipment are required to provide an optimal working interface between the operator and the cells (e.g., inverted microscope systems with high-power magnification, vibration isolation worktables, high-precision micromanipulators, etc.). All these individual pieces of equipment need to be acquired, assembled together and maintained. Additionally, even with functional equipment, the isolated measurement area is not readily accessible for fluorescence measurements or physical contact measurement methods (e.g. atomic force microscopy, scanning probe microscopy), making the conventional patch-clamp challenging to combine with other techniques.

To overcome some of these limitations, several advances have been made by adapting the patch-clamp technique to a planar surface containing multiple recording sites. Generally, automated planar patch-clamp systems can nowadays achieve high-throughput levels of data production in whole-cell and cell-attached recording modes without the need for a microscope, for a vibration isolation table, or for micromanipulators. Furthermore, intracellular and extracellular solutions can be controlled in such systems.

However, none of the planar patch-clamp systems provide the total versatility of the conventional patch-clamp setup. For example, excised patches are still only possible using micropipettes, and current planar chip technologies do not address this need. Additionally, they also require that cells first be resuspended in solution prior to being able to make measurements. These shortcomings limit the types of measurements as well as cell types that can be utilized, thereby restricting the number of users who could benefit from the technology.

Automated patch-clamp robotic systems utilizing micropipettes also exist, but are expensive and are not suitable for high-throughput data collection.

SUMMARY OF THE INVENTION

According to an aspect of the invention, there is provided a patch-clamp chip for making electrical measurements on a biological sample, the patch-clamp chip comprising a plurality of layers comprising poly-dimethylsiloxane (PDMS) and forming a stack, the plurality of layers comprising:
a chip surface layer extending in a plane and forming a surface of the patch-clamp chip, the chip surface layer comprising an aperture formed therethrough and which upwardly opens on the surface, where the biological sample is provided;
a microfluidic channel layer comprising a layer body made of PDMS, extending parallel to the plane and below the plane of the chip surface layer, the microfluidic channel layer comprising a microfluidic channel formed therein, wherein the aperture of the chip surface layer downwardly opens on the microfluidic channel.

According to an embodiment, the chip surface layer comprises a plurality of apertures, each of the apertures defining a recording site and which upwardly opens on the surface, each recording site being for receiving the biological sample.

According to an embodiment, the microfluidic channel layer comprises a plurality of microfluidic channels, comprising one microfluidic channel for each one of the apertures.

According to an embodiment, the plurality of microfluidic channels do not intersect with each other in the microfluidic channel layer, thus being independent from each other.

According to an embodiment, there is further provided at least two top electrodes deposited onto the chip surface layer about each of the apertures.

According to an embodiment, there is further provided a patterned electrically conductive layer under the microfluidic channel layer comprising a bottom electrode.

According to an embodiment, the bottom electrode has a top coating made of Ag/AgCl for electrical contact.

According to an embodiment, the patterned electrically conductive layer is to be deposited on a substrate comprising an electrically insulating material.

According to an embodiment, the patterned electrically conductive layer is to be deposited on an underlayer of PDMS to avoid requiring a substrate thereunder.

According to an embodiment, each of the apertures is a hole extending through the chip surface layer and having a cylindrical shape or a conical shape.

According to another aspect of the invention, there is provided a method of fabrication of a stack of layers comprising poly-dimethylsiloxane (PDMS), the method comprising:
forming a current layer of PDMS on a previous layer of PDMS, or on a substrate if the current layer of PDMS is a first layer;
curing the current layer of PDMS formed on the stack along with the stack;
applying a photolithography mask and a radiation in the deep UV range on the current layer of PDMS to expose the current layer of PDMS with a desired pattern;
repeating the steps of forming and curing the current layer of PDMS and applying the photolithography mask and the radiation in the deep UV range for all layers;
developing the stack by placing the stack in a solution for dissolving the exposed patterns in all layers.

According to an embodiment, applying a photolithography mask comprises locating the photolithography mask over the current layer of PDMS to shape microfluidic channels the current layer of PDMS.

According to an embodiment, the solution comprises a 1:1 mixture of: NaOH in water, and an alcohol chosen among: propanol, ethanol or methanol.

According to an embodiment, applying the photolithography mask and the radiation in the deep UV range comprises, for an uppermost layer of PDMS, displacing a deep UV range isotropic light source at a distance away from the photolithography mask, thus forming a truncated cone aperture after developing the stack.

According to an embodiment, for an uppermost layer of PDMS, there is further provided a micropatterning for directing cellular growth thereon.

According to another aspect of the invention, there is provided a patch-clamp chip fabricated using the method of claim 11.

According to another aspect of the invention, there is provided a method of performing electrophysiological measurements on a biological sample using a patch-clamp chip, the method comprising:
depositing the biological sample onto a surface of the patch-clamp chip, on an aperture formed through a surface of the patch-clamp chip, thereby forming a giga-Ohm seal between the biological sample and the aperture;
performing an electrical measurement between a microfluidic channel toward which the aperture downwardly opens, and a surface of the patch-clamp chip.

According to an embodiment, depositing the biological sample comprises depositing a plurality of biological samples on a corresponding plurality of apertures on the surface of the patch-clamp chip for performing simultaneous electrophysiological recordings of the plurality of biological samples.

According to an embodiment, the plurality of apertures each downwardly open toward a corresponding one of a plurality of microfluidic channels, wherein performing the electrical measurement comprises, for each one of the simultaneous electrophysiological recordings, connecting an electrical measurement apparatus:
to an electrical measurement apparatus to an external electrode connecting to one of the plurality of microfluidic channels; and
to a common ground electrode located in the bath compartment containing the surface of the chip,
for performing the simultaneous electrophysiological recordings of the plurality of the biological samples independently from each other.

According to an embodiment, the biological sample is a cell and wherein performing the electrophysiological measurements comprises performing one of: cell-attached mode, perforated patch mode, and whole-cell mode patch-clamp recordings.

According to an embodiment, the plurality of apertures each downwardly open toward a corresponding one of a plurality of microfluidic channels, wherein performing the electrical measurement comprises, for each one of the simultaneous electrophysiological recordings, connecting an electrical measurement apparatus:
to a bottom electrode in a bottom portion of each one of the plurality of microfluidic channels; and
to a common ground electrode located in the bath compartment containing the surface of the chip, for performing the simultaneous electrophysiological recordings of the plurality of the biological samples independently from each other.

According to an embodiment, the biological sample is a cell and wherein performing the electrophysiological measurements comprises performing excised-patch mode patch-clamp recordings.

According to an embodiment, performing excised-patch mode patch-clamp recordings comprises providing top electrodes on the surface of the patch-clamp chip by each one of the plurality of apertures which generate an alternating electric field to produce an excised patch.

According to an embodiment, the biological sample is one of: an organoid and a slice of organic tissue, or a lipid bilayer.

According to an embodiment, the surface of the patch-clamp chip comprises poly-dimethylsiloxane (PDMS).

According to an embodiment, the step of depositing the biological sample comprises culturing, incubating, or growing the biological sample on the surface of the patch-clamp chip.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1A:
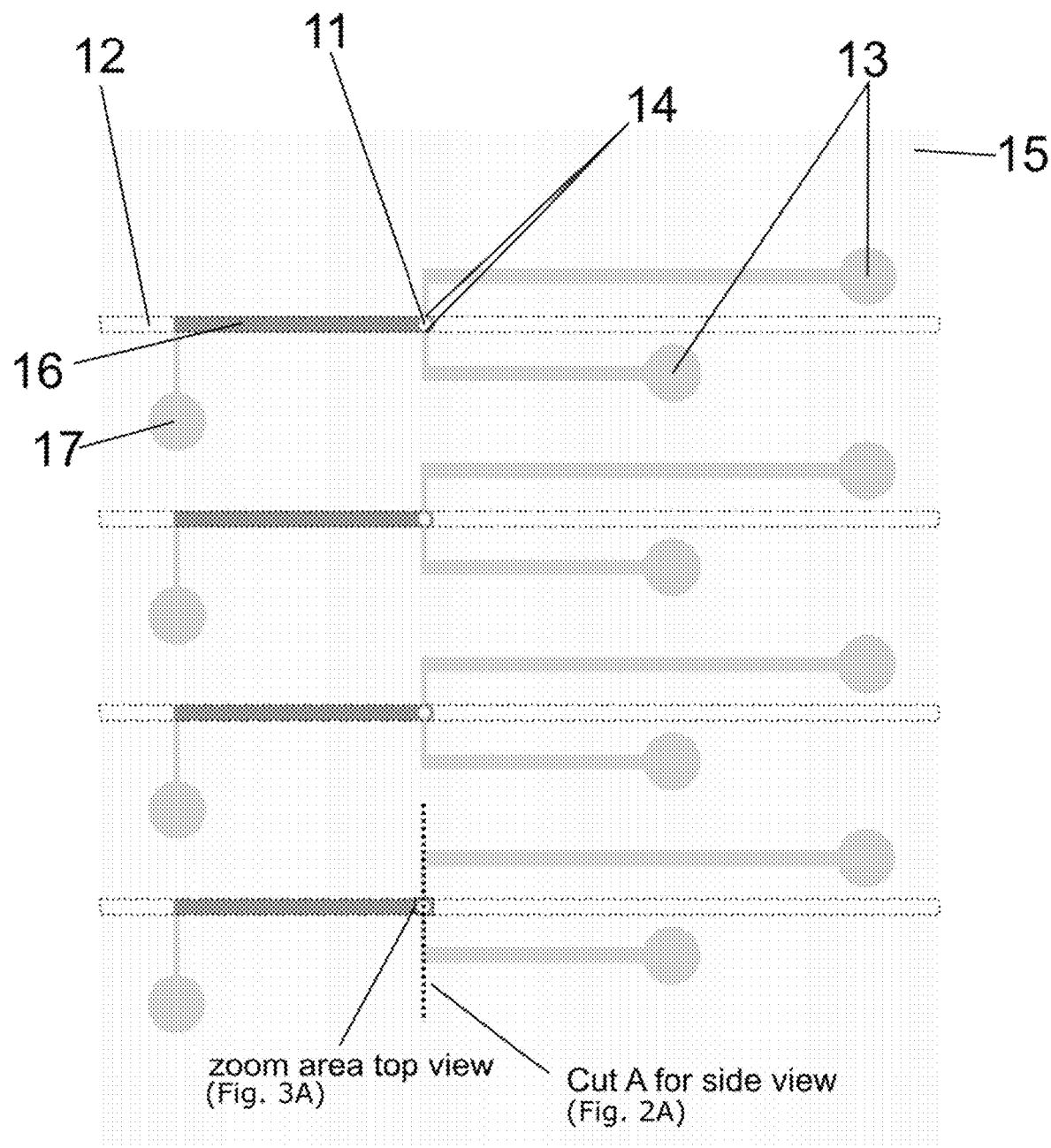
FIG. 1A is a top view illustrating a patch-clamp chip with four recording sites, according to an embodiment comprising bottom electrodes and contacts therefor as well as top electrodes and contacts.

To render patch-clamp generally more flexible and accessible to both research laboratories and to the industry, a versatile system that can be used like a plug-and-play device and still provide high-throughput, high-quality data would be a significant step to improve the patch-clamp technique. The present invention makes use of microfabrication techniques as a valuable option to mass produce new designs for more versatile patch-clamp chips. By making use of procedures developed within the semiconductor industry, silicon chips can be produced for patch-clamp applications. However, silicon has a high density of free charge carriers, potentially causing significant problems for sensitive electrophysiological recordings (e.g., transient parasitic current). Glass is a good insulator and can be used for patch-clamp chips, but the fabrication of glass-based chips is not as standardized as for silicon.

Processes are much simpler using polymers, as they are generally compatible with the use of standard fabrication techniques such as micro-molding. As part of this category, poly-dimethylsiloxane (PDMS) was found to be a candidate for patch-clamp chips. A disadvantage of PDMS, however, like other thermocurable polymers (i.e., cured by an elevation in their temperature), is the difficulty to manufacture parts with thin layers (on the order of 1-100 μm), comprising small and complex internal features. Multilayer PDMS parts are also subject to misalignment between layers due to shrinkage issues.

The present invention provides a chip, made from a stack of polymer layers with some of these layers comprising (micro) channels formed therein, for electrically and physically isolating a portion of a cell membrane. This chip notably enables high-throughput patch-clamp measurements to be taken, in multiple different configurations such as excised patch, whole-cell, perforated cell, and cell-attached recording modes. Cells are cultured directly on the chip, avoiding any requirements for cells to be resuspended in solution. This particularity allows experiments to be performed using more sensitive cell types (e.g., on neurons), in addition to tissue sections, acute tissue slices, organotypic cultures, and organoids. Experiments involving lipid bilayers instead of whole cells located at the recording site are also possible.

The chip according to the invention can be made of transparent materials, making it compatible with optical measurements of the isolated membrane area and optical observations of the cultured cells. The chip is designed such that the solutions on either side of the isolated membrane can be accessed.

According to an embodiment, the chip can comprise multiple recording sites, which can be connected to an electrophysiology acquisition system using conductive contacts on the chip (or chips) and/or conductive saline solutions together with appropriate electrodes (e.g. Ag/AgCl electrodes). This makes the patch-clamp chip particularly well adapted for automating simultaneous or sequential electrophysiological recordings of multiple patches. The present invention also includes the method for isolating a defined area of cell membrane as well as a method for fabricating the chip. This involves a method of microfabrication, described further below, for a multilayer poly-dimethylsiloxane (PDMS) object with internal and external features, which can be both micrometer-sized and complex in shape. This method of microfabrication overcomes the drawbacks mentioned above regarding the difficulty to manufacture parts with thin PDMS layers.

The present invention includes a PDMS-based patch-clamp chip designed to allow the functional versatility, flexibility and recording quality of the conventional patch-clamp technique, but with the possibility of collecting large volumes of data (high-throughput compatible), a control over internal and external solutions, as well as an optical access for high-resolution microscopy measurements. It also allows for the direct culturing of cells on the chip surface, eliminating the need to resuspend cells, thereby enabling experiments to be performed on sensitive cell types, such as neurons. It also comprises the associated methods and more specifically a procedure to achieve various patch-clamp configurations on-chip by electrically and physically isolating a definite portion of cell membrane. It also includes the related methods of fabrication, which can be applied to the fabrication of a multitude of devices, even unrelated to the present patch-clamp chip.

Patch-Clamp Chip and its Fabrication

The patch-clamp chip is composed of multiple layers and can have a single patch-clamp site or as many as the size and design of the chip allows for, as shown in FIGS. 1A, 1B, 2A, 2B, 3A, 3B.

Figure 1B:
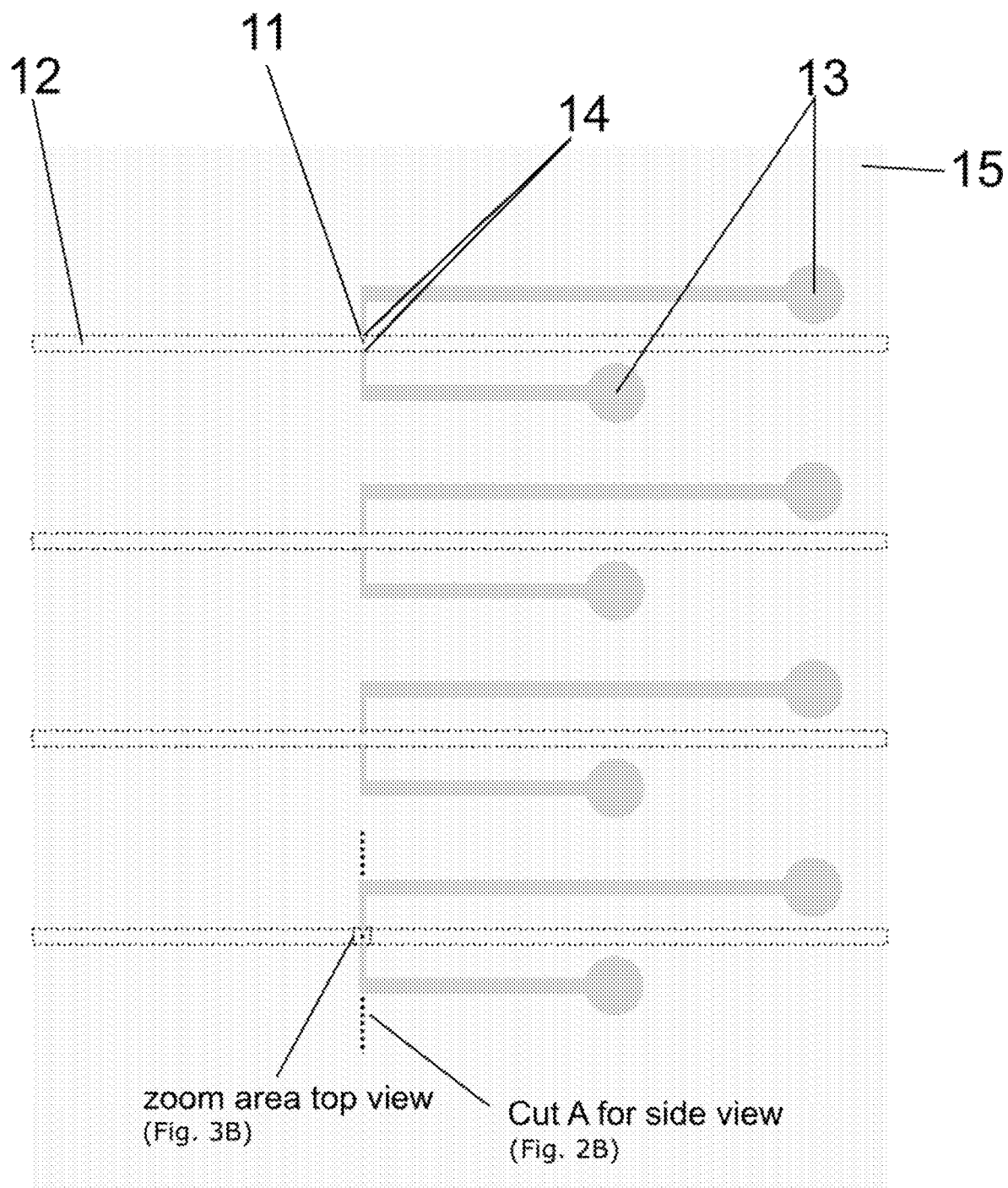
FIG. 1B is a top view illustrating a patch-clamp chip with four recording sites, according to another embodiment without bottom electrodes.
Figure 2A:
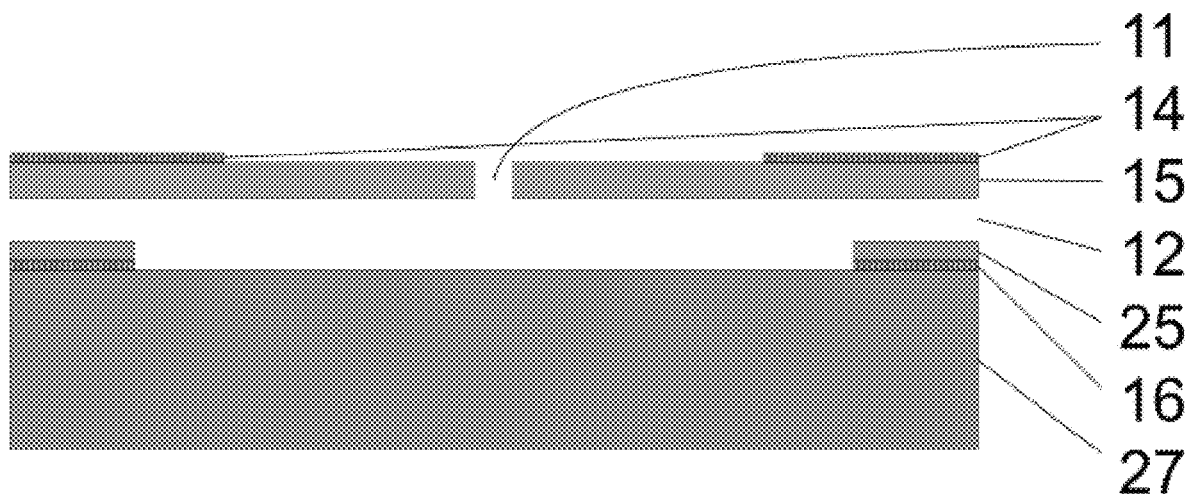
FIG. 2A is a side cross-section illustrating a portion of the patch-clamp chip of FIG. 1A, around a recording site.
Figure 2B:
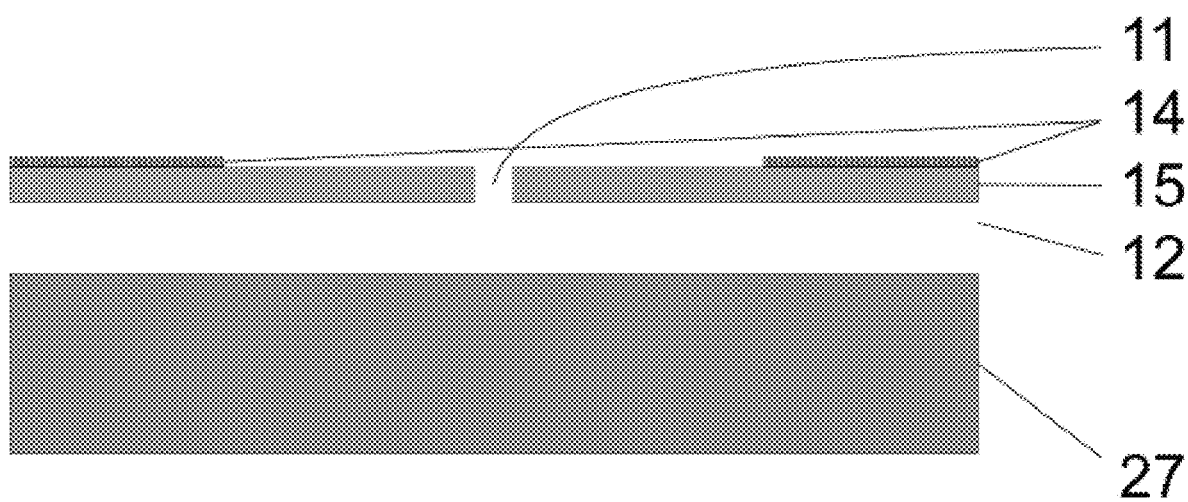
FIG. 2B is a side cross-section illustrating a portion of the patch-clamp chip of FIG. 1B, around a recording site.

FIGS. 1A and 1B are top views of a patch-clamp chip according to an embodiment containing 4 recording sites. The individual chip components are each indicated for one of the four recording sites shown. The three other recording sites have identical components as the indicated one. Side views of the cross-section around a recording site is shown in FIGS. 2A and 2B (related to FIGS. 1A-1B, respectively), as indicated by the cut A on FIGS. 1A-1B. Also, a close-up top view of the area around a single recording site is provided in FIGS. 3A and 3B (also related to FIGS. 1A-1B, respectively), as indicated in FIGS. 2A and 2B.

The patch-clamp chip comprises, for each recording site, an aperture 11 which is specific to the recording site. The aperture 11 is a hole provided on the surface layer 15 of the patch-clamp chip and opening on both of the upper surface and lower surface of the surface layer 15, thus enabling a connection between the regions above and under the surface layer 15 comprising the aperture 11, as shown in FIGS. 2A-2B. A microfluidic channel 12 is connected to the recording site's aperture 11 and extends below the surface layer 15; the aperture 11 opens, at its lower end, toward the microfluidic channel 12, such that the microfluidic channel 12 connects under a recording site. The surface layer 15 is defined as being "above" the other layers, and cells are deposited on an "upper" surface thereof. These directional terms (above/below and upper/lower) are used for convenience and in relation to the figures, and should not be considered as limiting the chip to a single orientation with respect to the ground.

There are contacts 13 provided for the top electrodes 14. Although there are two top electrodes 14 shown, there could be multiple top electrodes 14 (i.e., more than 2).

There is further provided a chip surface layer 15. Depending on the embodiment, the chip surface layer 15 can be made of PDMS, or functionalized PDMS, or glass deposited on the PDMS, or any other material to bind to PDMS permitting the culture of cells and/or achieving a giga-Ohm seal in the recording site aperture 11. The chip surface layer 15, made of PDMS or other materials as described above, is the layer in which the aperture 11 is provided, as shown in FIGS. 2A-2B.

Figure 3A:
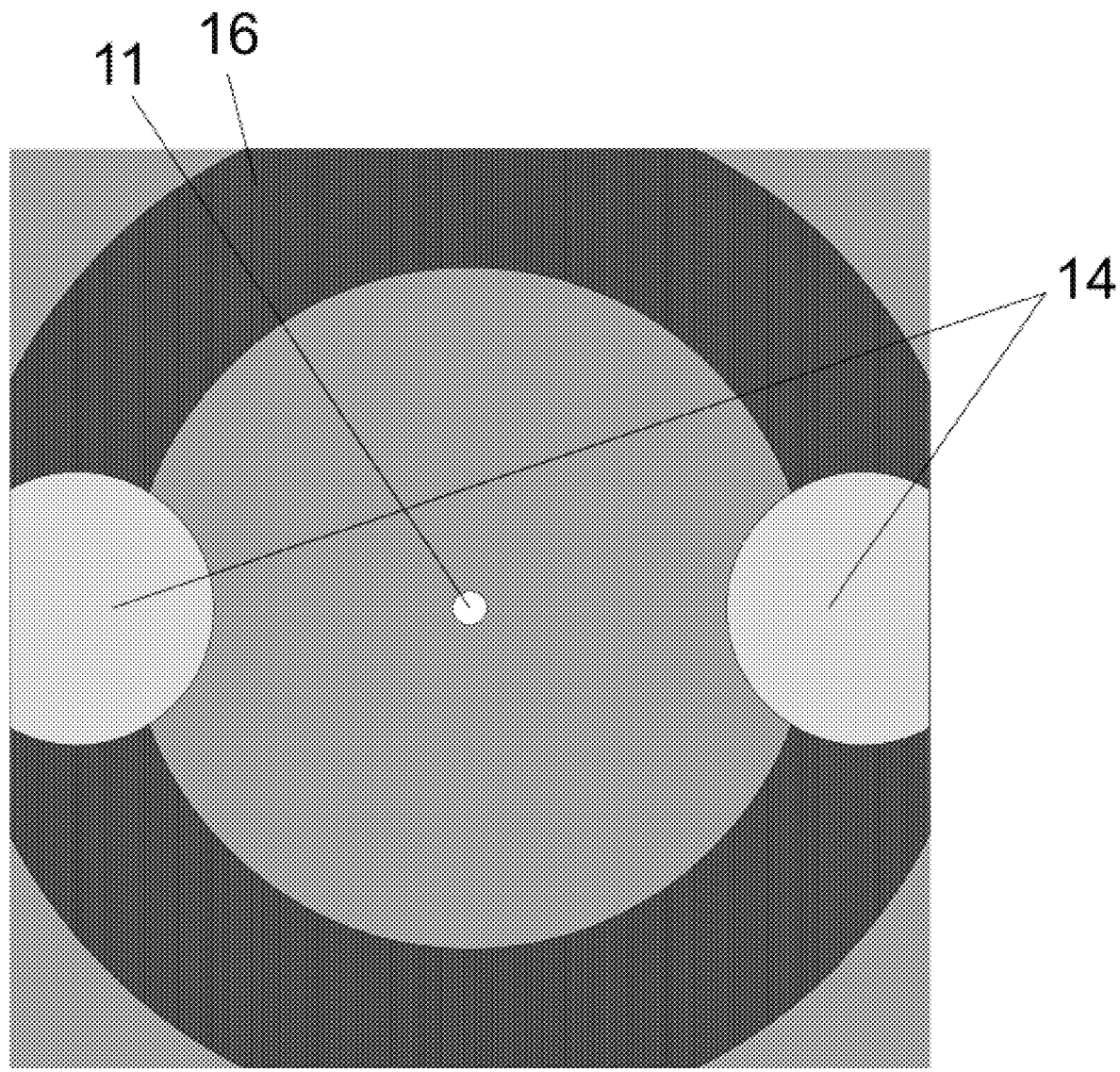
FIG. 3A is a top view illustrating a portion of the patch-clamp chip of FIG. 1A, around a recording site.
Figure 4A:
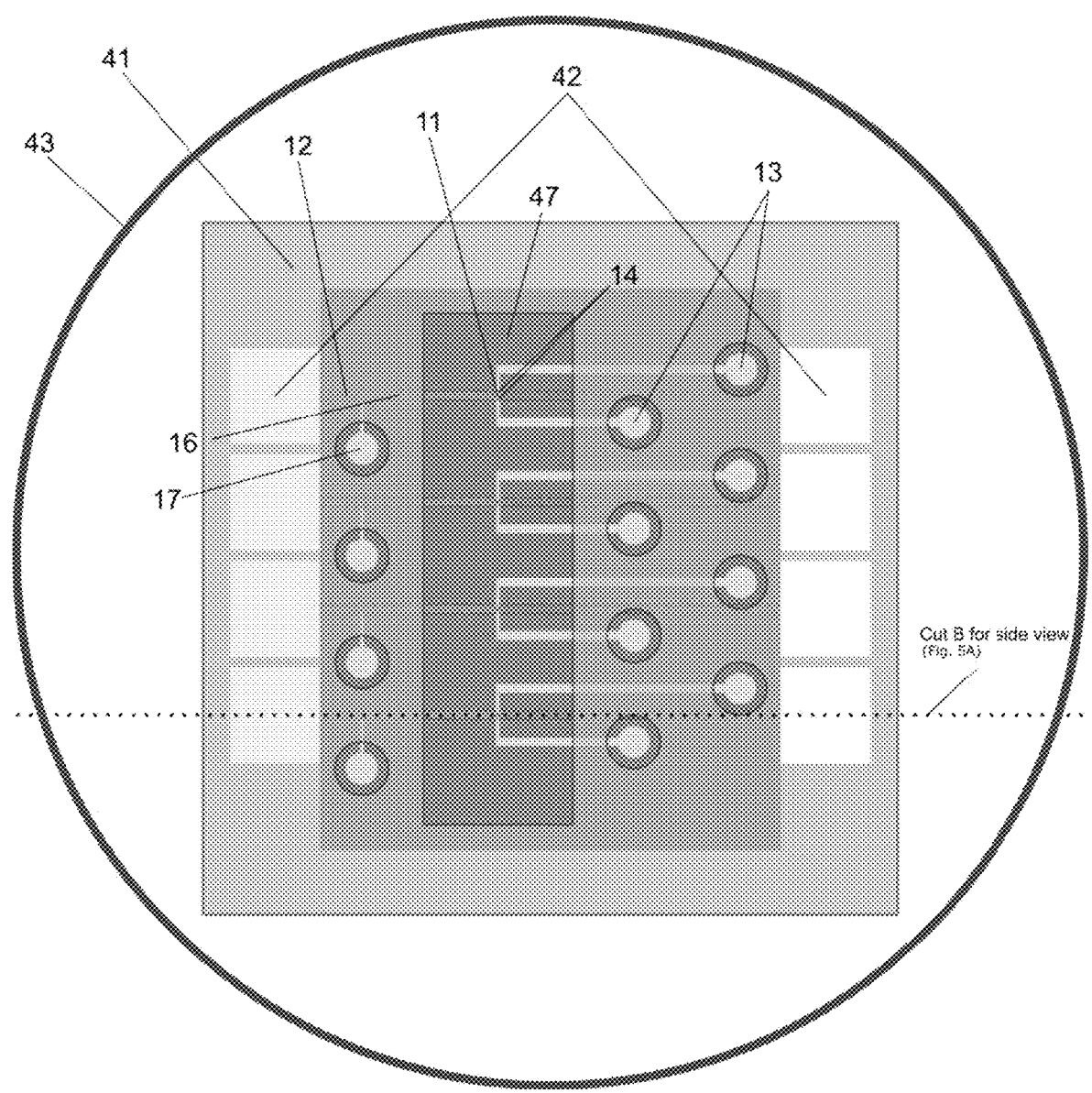
FIG. 4A is a top view illustrating a patch-clamp chip with four recording sites and a top adapter, according to an embodiment comprising bottom electrodes and contacts therefor as well as top electrodes and contacts.

Moreover, the patch-clamp chip can comprise a bottom electrode 16 with a top coating of a material known to provide a suitable recording electrode for electrophysiological measurements. In an exemplary embodiment, this material would comprise Ag/AgCl, thus forming a silver chloride electrode. In FIG. 4A, there is further shown a contact 17 for the bottom electrode 16. FIGS. 1A, 2A and 3A also relate to this particular embodiment comprising a bottom electrode 16 and its contact 17.

Alternatively, a recording electrode outside of the chip can be connected directly from the amplifier system to the internal solution of a microfluidic channel 12. In such case, the bottom electrode 16 is not included in the fabrication process of the chip. FIGS. 1B, 2B, 3B and 4B are directed to this particular embodiment without the bottom electrode 16 and its contact 17.

FIGS. 2A and 2B are a close-up view of the cross-section of the patch-clamp chip, as indicated in the cut A of FIGS. 1A and 1B, illustrating the components of the area around a recording site. Each of the components are described as follows. The surface layer 15 is illustrated. The aperture 11 of the recording site is shown to extend through the surface layer 15. Again, the top electrodes 14 are shown (two of them are shown, but a greater number of top electrodes 14 could also be provided). A microfluidic channel 12 is shown in FIGS. 2A and 2B. The bottom electrode 16 is illustrated in FIG. 2A. A top coating 25 of a material known to provide a suitable electrode for electrophysiological measurements is shown. In an exemplary embodiment, this material would comprise Ag/AgCl, which provides a bond to the bottom electrode 16. The top coating 25 is not provided in embodiments where the bottom electrode 16 and its contact 17 are absent.

Figure 5A:
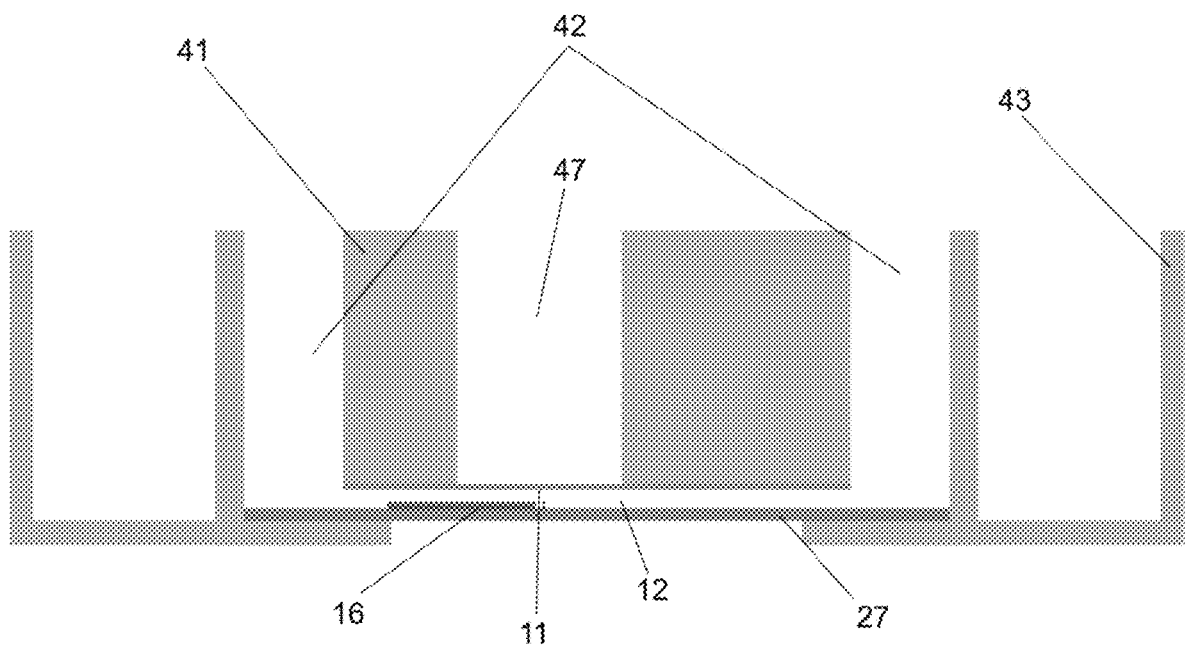
FIG. 5A is a cross-section illustrating the patch-clamp chip of FIG. 4A with a top adapter.
Figure 5B:
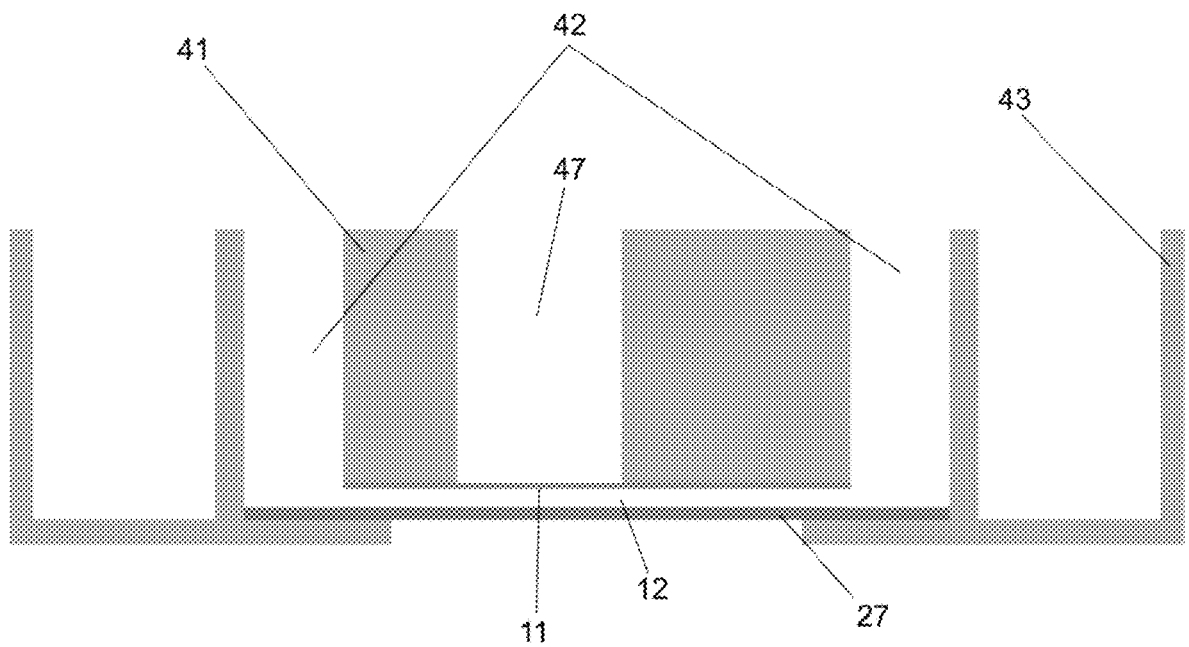
FIG. 5B is a cross-section illustrating the patch-clamp chip of FIG. 4B with a top adapter.

A substrate 27 is also indicated in FIGS. 2A-2B and 5A-5B, and can be the substrate for the bottom electrode 16. In one embodiment, the substrate 27 is made of glass. As shown in FIGS. 2B, 5B, it can be present even for the embodiment without the bottom electrode 16.

Figure 3B:
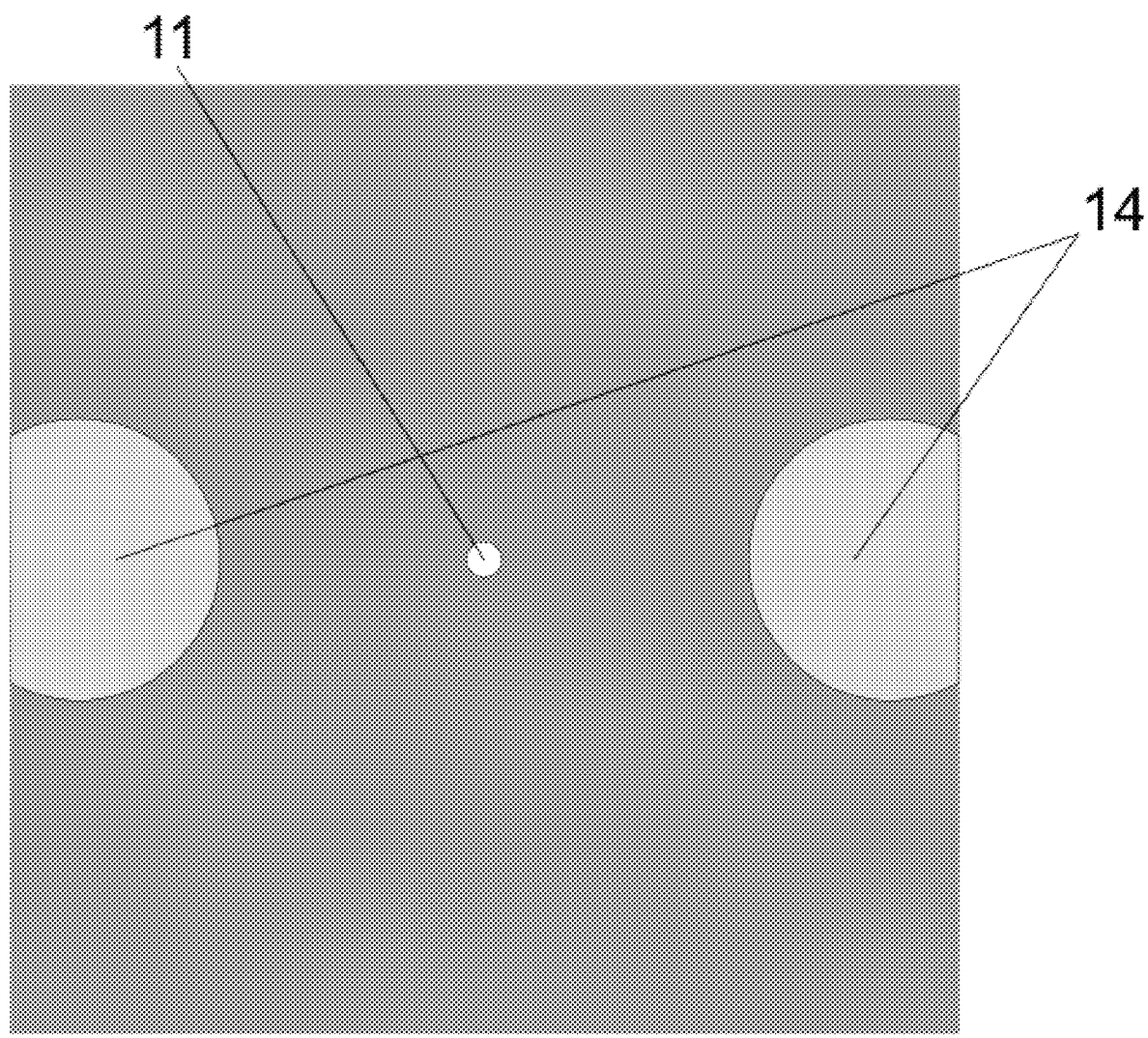
FIG. 3B is a top view illustrating a portion of the patch-clamp chip of FIG. 1B, around a recording site.

FIGS. 3A and 3B are top views showing the zoomed area of the patch-clamp chip around a recording site as indicated in FIGS. 1A and 1B. Again, the aperture 11 of the recording site is shown. The bottom electrode 16 is also illustrated in FIG. 3A, along with a top coating 25 made of a material known to provide a suitable electrode for electrophysiological measurements (e.g. Ag/AgCl). The top electrodes 14 are also illustrated.

As seen from FIGS. 2A and 2B, the patch-clamp chip comprises multiple layers, which are now described more formally below (referring to layers 1 to 5).

First Layer

Starting from the bottom, the first layer comprises the substrate 27 upon which the other layers are added. The substrate 27 can be made from one of several different kinds of insulating material, and it needs to bind to PDMS to achieve the multilayer PDMS-based system.

In one embodiment, the substrate 27 can be made of glass, and the transparency allows for optical access to the patch site, i.e., it can be viewed by a person or by measurement instruments. The thickness of the substrate 27 can be chosen to suit the needs of high-resolution microscopy or any other types of optical measurements.

According to another embodiment, the substrate 27 can be made in a material other than glass, especially if optical transparency is not required for a specific application not involving microscopy. In this case, the glass may be replaced by another electrically-insulating material to receive the electrically-conductive patterned layer thereon. Such electrically-insulating material can include, in addition to glass, various types of plastics, or rubber, or other suitable polymers.

Second Layer

The second layer (from the bottom) comprises a patterned electrically conductive layer, comprising the contacts and the associated electrodes (e.g., bottom electrode 16 and its contact 17 for each recording site) located under the recording sites, in the microfluidic channel 12. In one embodiment, the second layer can be deposited directly onto the substrate 27, as shown in FIGS. 2A, 5A, with the bottom electrode 16 direct deposition thereon.

In another embodiment, there could be PDMS deposited onto the substrate 27 to provide an underlayer to the conductive layer. This second embodiment could allow, for example, a malleable version of the patch-clamp chip to be produced, that does not contain substrate 27 when manufactured. The type of conductive layer is chosen to provide an electrical connection to an electrode suitable for electrophysiological measurements (e.g. the top coating, thereof made of Ag/AgCl) and make good electrical contacts to an external system connecting to the patch-clamp chip. This electrode is herein defined as the bottom electrode 16, referring to its location relative to the recording sites. It can be of any thickness, but a sub-micrometer thick layer is sufficient. If the chip connects electrically to an external system, the contacts 17 for the bottom electrodes 16 remain accessible from the top and are isolated from solutions, as shown in FIG. 4A. However, if the chip connects directly to another chip device, it is possible to combine the design of both chips and establish a connection between the two systems without the need for contacts available for external systems.

If present in the chip, the bottom electrode 16 can be shaped and deposited onto substrate 27 (or alternatively onto PDMS if the substrate is absent from the initial manufacturing process) using standard microfabrication techniques. For instance, photolithography can be used to pattern the material of the bottom electrode onto substrate 27 (or alternatively onto PDMS). The material of the bottom electrode can be deposited using standard thin film deposition methods such as physical vapor deposition (e.g. sputtering, evaporation).

Since silver/silver chloride (Ag/AgCl) is generally chosen for electrophysiological recordings, the bottom electrode 16 can be made of an Ag layer, for instance. An AgCl layer can be formed on the desired area by electroplating or other standard procedures such as soaking the silver in chloride solution. This AgCl layer bonded to the bottom electrode 16 provides a suitable electrode for electrophysiological measurements. The bottom electrode 16 could also be made of gold, for example, because of its high resistance to corrosion. AgCl can then be electrodeposited thereon. The shape of the electrode can be adapted to surround the recording site, thereby helping the user to find the position of the recording site and maintain good optical access of the recording site (FIG. 3A).

In another embodiment, as mentioned above, the bottom electrode 16, therefore the second layer, can be omitted. When the chip is used, users can simply add an external electrode or a connection to an electrode (e.g., agar salt bridges) directly to the internal solution (e.g., compartment 42) going through a microfluidic channel 12 connecting under a recording site. This could be done prior to an experiment (FIG. 1B, 2B, 3B, 4B).

Third Layer

In a third layer, a PDMS layer comprising the microfluidic channels 12 is placed between the bottom electrodes 16, if any, or between the substrate 27 and the recording sites to allow solution exchange under the recording sites. The number of independent microfluidic channels 12 corresponds to the number of independent recording sites. The independent microfluidic channels 12 can run parallel to each other, or may not be exactly parallel but at least should not intersect with any other one. The absence of intersection between the microfluidic channels 12, for example by preserving a wall between each pair of adjacent microfluidic channels, makes them independent from each other and allow the eventual electric measurements to be independent for each recording site/aperture 11.

Each biological sample deposited onto a recording site can undergo an electrophysiological measurement independently since they have dedicated microfluidic channels 12 receiving an independent electrical measurement, either via the bottom electrode, or by direct electric connection of an electrical measurement apparatus with the internal solution in the microfluidic channels 12. The external solution on the surface of the chip is connected to a common electrical ground signal. According to an embodiment, a ground electrode is placed in the compartment 47 (common electrical ground for all measuring sites) and the measuring electrode can be the bottom electrode 16 or an Ag/AgCl wire connecting to the internal solution in the microfluidic channel 12.

The size of the channel can vary depending on the desired flow of solution. The channels can be linked, for instance, to baths located outside the substrate (FIG. 4A, 4B) or to ports passing through the PDMS allowing for the connection of tubing directly to the chip. If no solution exchange is desired below the recording site, a small container feeding the microfluidic channel can be used instead.

This third layer can be fabricated, for instance, using standard soft-lithography methods (i.e. molding of PDMS and adhesion to the previous layer), or for purposes of greater resolution, by using the fabrication method described below (see "Method for building high-resolution PDMS multilayer devices"). If the latter method is used, the PDMS layers are exposed following the pattern of the microfluidic channels or the tank area under the recording site, as well as the contacts of the bottom electrodes if contacts are required to remain accessible from the top of the chip. Exposed areas are then removed to form the desired features within a body of PDMS material.

Figure 4B:
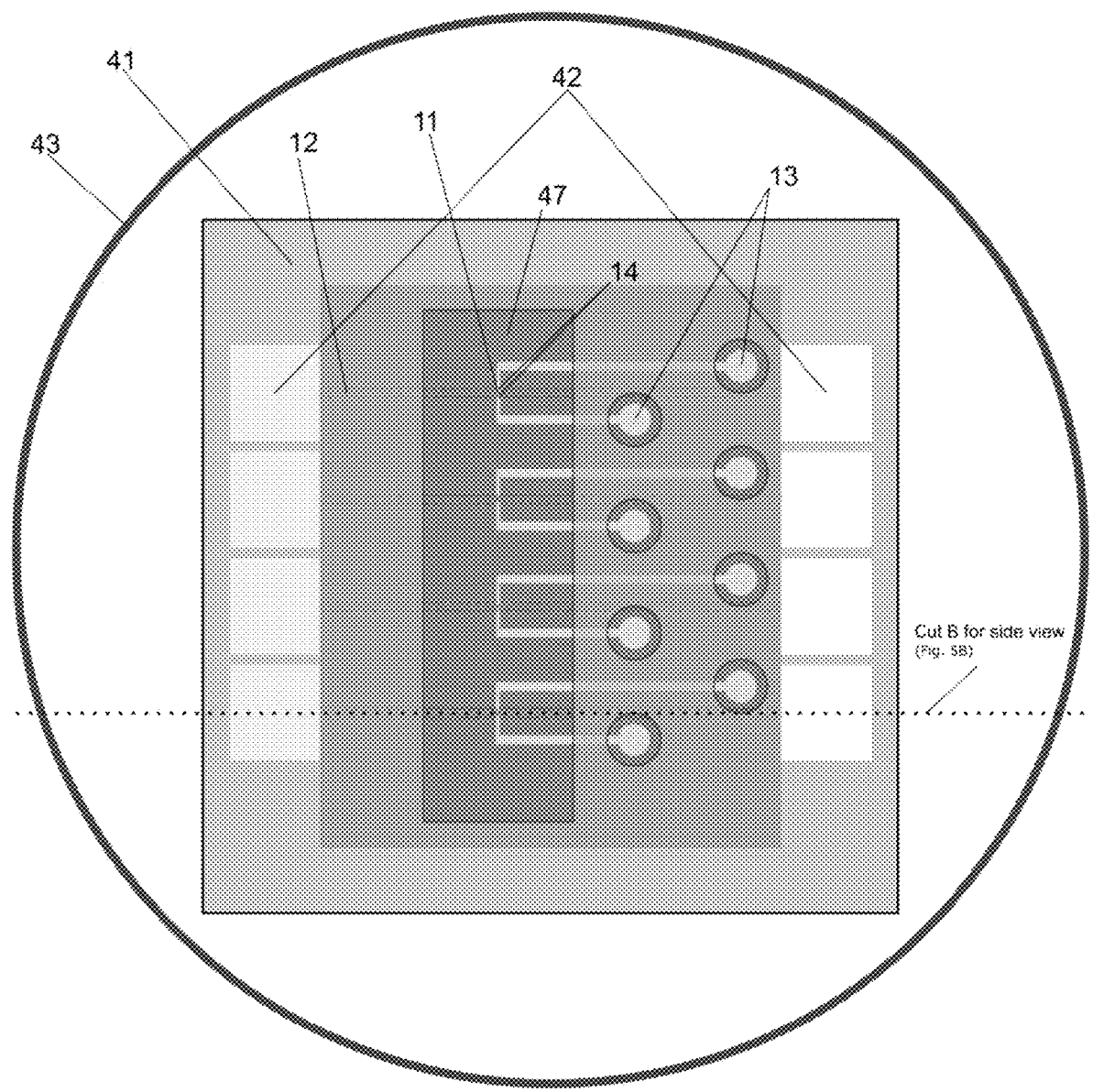
FIG. 4B is a top view illustrating a patch-clamp chip with four recording sites and a top adapter, according to another embodiment without bottom electrodes.

FIGS. 4A and 4B are top views of one embodiment of a patch-clamp chip with four recording sites, as indicated in FIGS. 1A and 1B, but with an adapter over the chip to isolate contacts 13 and 17 from the solution compartments 42 and 47. FIGS. 5A and 5B are cross-sections of cut B indicated in FIGS. 4A and 4B, respectively. The chip components are shown for only one of the four recording sites. The three other recording sites have identical components and are not shown. The top adapter 41 is provided to isolate the contacts and the solutions in the defined compartments 42 and 47. The compartments 42 are illustrated and confine the solution for their respective microfluidic channel 12. As indicated, the chip is supported by the chamber support 43. A microfluidic channel 12 is connected to the recording site, or aperture 11. A top chamber 47 is provided to contain the bath solution and cells. Top electrodes 14 are provided, and so are the bottom electrodes 16 (FIG. 4A, not 4B where layer 2 is excluded) with a top coating 25 of a material known to provide a suitable electrode for electrophysiological measurements (e.g. Ag/AgCl). Furthermore, there are contacts 13 for the top electrodes 14 and contacts 17 for the bottom electrode 16 provided (FIG. 4A, not 4B where layer 2 is excluded). Holes 42 within the top adapter 41 allows the contacts to be accessible using external connectors.

FIGS. 5A and 5B, mentioned above, are side views of the chip at the line defined by cut B as indicated in FIGS. 4A and 4B, respectively. The aperture 11 of the recording site appears in the PDMS layer, and the microfluidic channel 12 is shown as being connected to the recording site, or aperture 11.

Layer 4

The fourth layer is the chip surface layer 15 preferably made of PDMS (or any equivalent material mentioned above) including apertures 11 where an area of a cell membrane is isolated (i.e. the recording sites), and is over the third layer which is the PDMS layer containing the microfluidic channels 12. The aperture 11 can be of any size and shape, but preferably round (from a top view) with a diameter of about one micrometer, thus forming a cylindrical or conical hole through the chip surface layer 15. Through the PDMS layer, the aperture can be made straight or conical (from a side view).

Up to that layer, i.e., without the fifth layer described below, the chip can be used for cell-attached and whole-cell mode patch-clamp recordings. Indeed, to operate the chip under these patch-clamp configurations, the chip can be made without the bottom electrode 16, as discussed above, and also without the top electrodes 14 (e.g., as shown in FIG. 2B for example, without the electrode 14).

This fourth layer can be fabricated as is described for the fabrication of the third layer (preferably using the method of microfabrication described below), but with the pattern of the apertures, as well as the contacts of the bottom electrodes, if contacts are required to remain accessible from the top of the chip.

In one embodiment, layer 4 can also be functionalized, or made from another material, (provided this material permits cells to be cultured and for giga-ohm seals to be attained in the recording site aperture 11) that can be deposited on top of that chip surface layer 15.

Fifth Layer

The fifth layer is a patterned electrically conductive layer, comprising the at least two top electrodes 14 per recording site and their associated contacts, which can all be placed over the fourth layer. The fifth layer provides a way to obtain excised patches (i.e. a patch with only the area of the membrane in the aperture being isolated, without the rest of the cell), while it is not present for cell-attached and whole-cell mode patch-clamp recordings. These electrodes are defined as the "top" electrodes 14, referring to their position relative to the aperture of the recording sites. The top electrodes can be of any thickness, but a sub-micrometer thick layer is sufficient. The top electrodes can be made of a material that is not cytotoxic, and is chemically stable when exposed to the solutions used for cell culture or for electrophysiology recordings. The top electrodes 14 should also be of a material resistant to oxidation, to maintain their conductivity so that an electrical potential can be applied. In one embodiment, gold is used to produce the top electrodes 14. If the chip connects electrically to an external system, the contacts of the top electrodes 14 remain accessible from the top and are isolated from solutions (FIGS. 4A and 4B). However, if the chip connects directly to another chip device, it is possible to combine the design of both chips and establish a connection between the two systems without the need for contacts available for external systems. The top electrodes 14 can be shaped and deposited on the previous layer using standard microfabrication techniques, as is described, for example, for the bottom electrodes 16 of the second layer.

The top electrodes 14 are used not for electrophysiological measurements, contrarily to the bottom electrode 16 (or any other equivalent thereof). The top electrodes 14 are used to break portions of a cell, or cell membrane, located over the aperture 11 when going from a cell-attached configuration to an excised-patch configuration. According to an embodiment, there should be at least two of them, and a greater number is also possible. In practice, to perform the electrophysiological measurements, a ground electrode is placed in the compartment 47 (shown in FIGS. 4A-4B, common ground for all measuring sites) and the measuring electrode can be the bottom electrode 16 or an Ag/AgCl wire (or a wire made from another material allowing electrophysiological measurements) connecting to the internal solution in the microfluidics 12. Top electrodes 14 do not have an Ag/AgCl coating, which is required only for the bottom electrodes 16, if any. Since the top electrodes are not recording electrodes, they only need to be made of a material that is not cytotoxic and is chemically stable when exposed to the solutions used for cell culture or for electrophysiology recordings. (e.g., gold).

The top electrodes 14 can generate an alternating electric field to produce cell-membrane breakdown at the surface in proximity to an aperture 11 and keep a portion of the cell intact within the aperture for performing excised-patch mode patch-clamp recordings.

Patch-Clamp Chip Overview

The patch-clamp chip is designed to be flexible and versatile, like the conventional patch-clamp system, but compatible with high-throughput data collection paradigms and the ability to exchange solutions on both sides of the patch. Both academic and industrial research will benefit from this advance. A bottom electrode 16 or an external electrode connecting to the microfluidic channel 12 is used as the recording patch-clamp electrode, while the ground bath electrode, is connected to the bath on the surface of the chip where the cells are (FIGS. 4A and 4B). Also, with direct cell culture possible on the patch-clamp chip, cells do not need to be in suspension to be recorded, unlike with prior art techniques. This makes the whole process simpler, faster and allows cells which do not tolerate resuspension to be utilized.

Alternatively, instead of using whole cells, experiments with lipid bilayers are also possible with the chip described above. There is also a good potential for this advancement to allow recordings on organoids and tissue slices. With all its layers of transparent materials of controllable thickness, the patch-clamp chip can be used for standard optical measurements as well as high-resolution widefield microscopy. Moreover, because of its configuration, physical contact measurement methods (e.g., atomic force microscopy, scanning probe microscopy) are also possible.

Additionally, by having multiple recording sites on which culture of sensitive cells is allowed, the chip could be used for the study of neuronal networks as an alternative to the multielectrode arrays (MEAs). Patch-clamp can provide more precise and higher resolution data, so there is a certain potential to use patch-clamp chip instead of MEAs. Furthermore, the patch-clamp chip does not require the use of complex robotics or electronics. The contacts available can easily be used with connectors to establish an electrical connection with standard third-party patch-clamp acquisition systems. A switch, manual or electronic, can be installed in-between the patch-clamp chip contacts and the amplifier headstage to select any one of the recording sites at a given time, for the purposes of making sequential measurements. Otherwise, a multi-channel amplifier and acquisition system can be connected to record from all patch sites simultaneously, without the need of a manual switch.

Method to Achieve Various Patch-Clamp Configurations On-Chip by Electrically and Physically Isolating a Definite Portion of Cell Membrane The patch-clamp chip described in this invention can allow for electrophysiological measurements to be taken in whole-cell, cell-attached and excised patch configurations. Therefore, as opposed to prior art chip systems, the patch-clamp chip according to the invention is as versatile as the conventional, manual patch-clamp system while also having the advantages of a chip system, namely the possibility of high-throughput, the solution exchange for both intra and extra-cellular solutions and the compatibility with optical and physical contact measurements. Additionally, cells do not need to be put into suspension. Altogether, this system can be used for purposes other than patch-clamp. For instance, an excised patch on a chip with solution exchange can become a suitable platform for fluorescence experiments at the single-molecule level. Intracellular labeling can also be performed during an experiment. Atomic force microscopy (AFM) or scanning probe microscopy (SPM) can equally be applied to the cell membrane.

To achieve these characteristics of a versatile patch-clamp chip system, a cell forms an electric seal (a giga-ohm seal) on one of the apertures 11 (the recording sites), located between the bath solution and the respective microfluidic channel. This is known as cell-attached mode. From that moment, the electrodes of that recording site can be used to break certain areas of the cell membrane. For instance, whole-cell mode is often achieved on a conventional patch-clamp system by supplying short electrical pulses between the micropipette electrode and the bath electrode. The same principle can be applied in this chip configuration using the bottom electrode and a bath electrode over the surface of the chip. Electric field of various amplitudes and frequencies can also be applied to provoke the membrane breakdown.

Experiments with gold microelectrodes showed that membrane breakdown can be achieved on a planar surface at low voltage and close distance without much increase in temperature. This is now applied for patch-clamp applications to provide an electric field allowing the isolation of a portion of cell membrane. By breaking the membrane on the top side, an excised patch is achieved in the patch-clamp aperture 11. At least 2 electrodes are used around the aperture, but a larger number can be used to create, for instance a quadrupole around the aperture. Alternatively, by breaking the cell membrane within the aperture, whole-cell mode is achieved.

Method of Fabrication of High-Resolution PDMS Multilayer Devices

Layers of PDMS comprised in the patch-clamp chip must be fabricated with a sufficient spatial resolution to be able to achieve the desired result. Since the size of the microfluidic channels within the present chip is very small, they must be fabricated using a microfabrication process that can achieve sufficient resolution. Below, a method of microfabrication is described which addresses the need for high-resolution microfabrication of PDMS layers.

Figure 6:
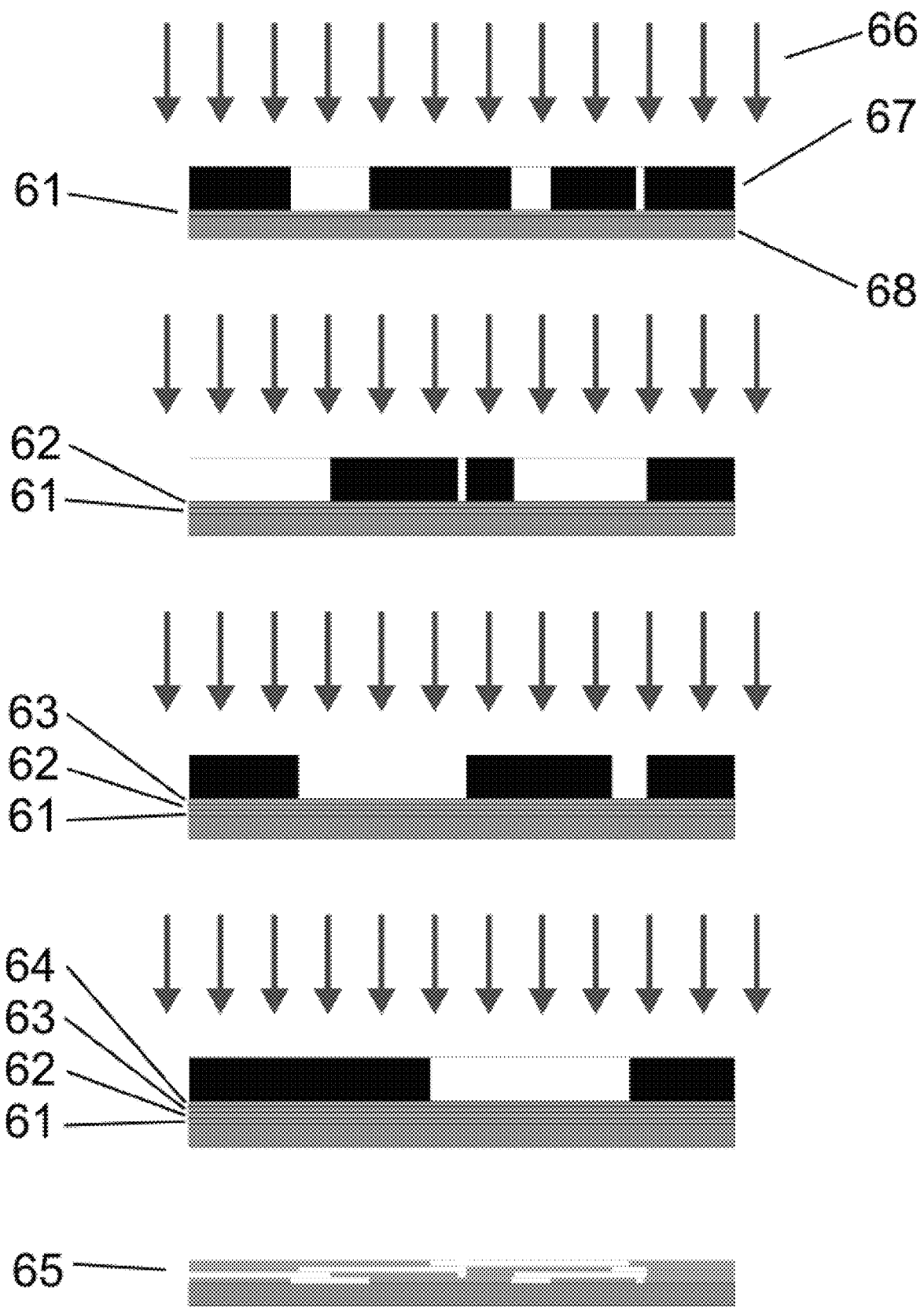
FIG. 6 is a series of schematic diagrams illustrating a method of fabrication of a high-resolution PDMS multilayer device, according to an embodiment.

A PDMS object with internal and external features is built from a stack of PDMS layers, each having a thickness of about 5-10 µm or slightly less and patterned using light according to the global 3D design of the object (FIG. 6). Unlike prior art techniques, this method according to an embodiment of the present invention does not require the bonding of previously-cured PDMS layers, and a layer can be added to the stack in its uncured form (liquid) by using methods such as spin coating. That layer is then cured together with the object being built.

The layer is then patterned using light of wavelengths in the Deep-UV range (about 200 nm or slightly below while remaining in the UV range, e.g., in practice, most mercury-based sources emit at 193 nm or 248 nm, which are suitable wavelengths), or smaller wavelengths, which follows the desired pattern. According to an embodiment, this is done using a photolithography mask. This exposure will affect the structural properties of PDMS within about 10 µm, depending on the dose of light (<200 nm) that has been applied. The wavelength of the radiation used for photolithography being small, it can achieve the desired spatial resolution (~1 µm).

This process is repeated for every layer until the stack is complete. A last step of development, which involves placing the stack in a solution, removes the exposed areas (those that were subject to photolithography by exposure to the deep UV radiation) of the object within all layers (and not only those on the surface), if the exposed areas are interconnected and if the developing solution can reach the exposed areas within the stack of layers via at least one entry point. This will allow for the exposed areas from all layers, after having been solubilized by the developing solution, to leave the object. A single development step is needed for the whole stack.

This allows the fabrication of complex internal and external features at high resolution within PDMS objects, and at a resolution that is sufficient for the layers comprising microfluidic channels as described above in relation with the patch-clamp chip.

According to one embodiment, a suitable development solution is a 1:1 mixture of NaOH in water and an alcohol chosen among: 2-propanol, ethanol or methanol.

FIG. 6 illustrates the method for building high-resolution PDMS multilayer devices. This example comprises four PDMS layers, labeled 61, 62, 63, 64 in order from bottom to top, sitting on a substrate 68. For each layer, a pattern is transferred using a photomask 67 and deep-UV light beam 66 produced by a deep-UV light source. After all layers get their patterned light exposure, the object is developed to produce the final PDMS multilayer object 65.

The process does not use molding and does not require bonding between layers, and therefore avoids shrinkage issues and other associated problems when bonding PDMS layers. This method takes advantage of simple photolithographic procedures, making it easily applicable to large scale production.

Figure 7:
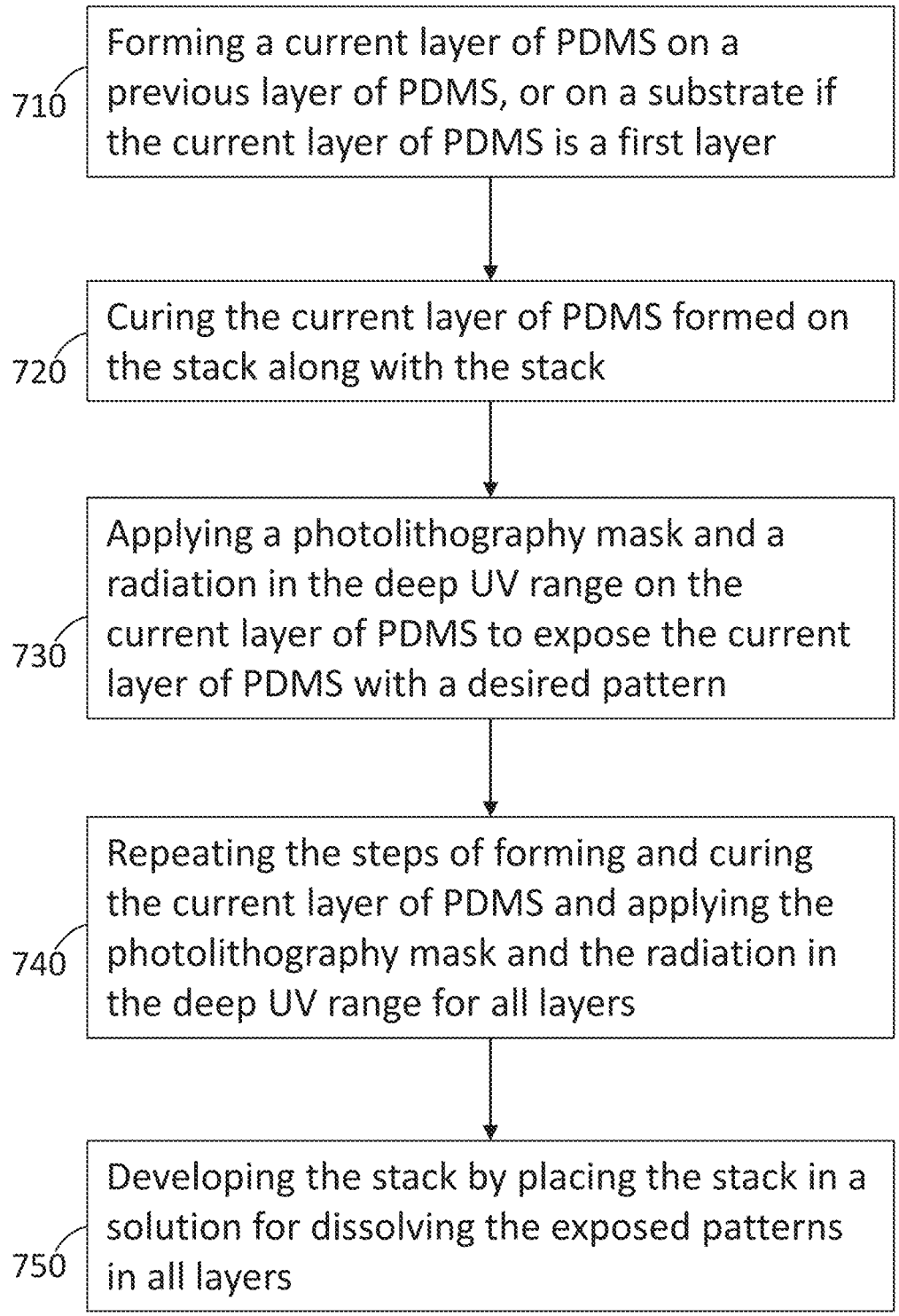
FIG. 7 is a flowchart illustrating a method of fabrication of a high-resolution PDMS multilayer device, according to an embodiment.

FIG. 7 is a flowchart illustrating a method of fabrication of a stack of layers comprising poly-dimethylsiloxane (PDMS), the method comprising:

Step 710: forming a current layer of PDMS on a previous layer of PDMS, or on a substrate if the current layer of PDMS is a first layer;

Step 720: curing the current layer of PDMS formed on the stack along with the stack;

Step 730: applying a photolithography mask and a radiation in the deep UV range on the current layer of PDMS to expose the current layer of PDMS with a desired pattern, such as the microfluidic channels 12 or the apertures 11;

Step 740: repeating the steps of forming and curing the current layer of PDMS and applying the photolithography mask and the radiation in the deep UV range for all layers; and Step 750: developing the stack by placing the stack in a solution for dissolving the exposed patterns in all layers.

According to an embodiment, in order to create the aperture with the desired shape (such as a cylinder or truncated cone section), a deep-UV lamp (i.e., deep-UV range light source) having isotropic light emission is placed to a given distance from the mask or from the substrate under exposure. The portion of PDMS material being exposed corresponds to an aperture to be formed, and this portion under exposure, through the thickness of the layer, has a cone shape (or more formally, a truncated cone section). The cone shape, and the inclination of the sides forming said cone shape, can be modulated by varying the distance between the lamp and the mask/substrate. An extreme case would include a truncated cone section defined by walls that are substantially parallel, hence the cylindrical shape. By doing so, the resulting device allows better control of the position of the cell membrane where the seal occurs (expected around the smallest diameter). There may also be an impact on the strength of the seal and overall good working of the electrical measurements on the cell membrane.

According to an exemplary embodiment, the chip surface may undergo additional treatment, in particular, a micropatterning treatment on the chip surface layer 15. This micropatterning would make the cells grow naturally on the chip surface layer 15, but the directions according to which they would grow would be driven by certain geometrical patterns formed by the micropatterning treatment. For example, the micropatterning treatment can include a pattern formed by chemicals deposited onto the surface and linked thereto; such chemicals would promote cell growth along the pattern form by them.

Figure 8:
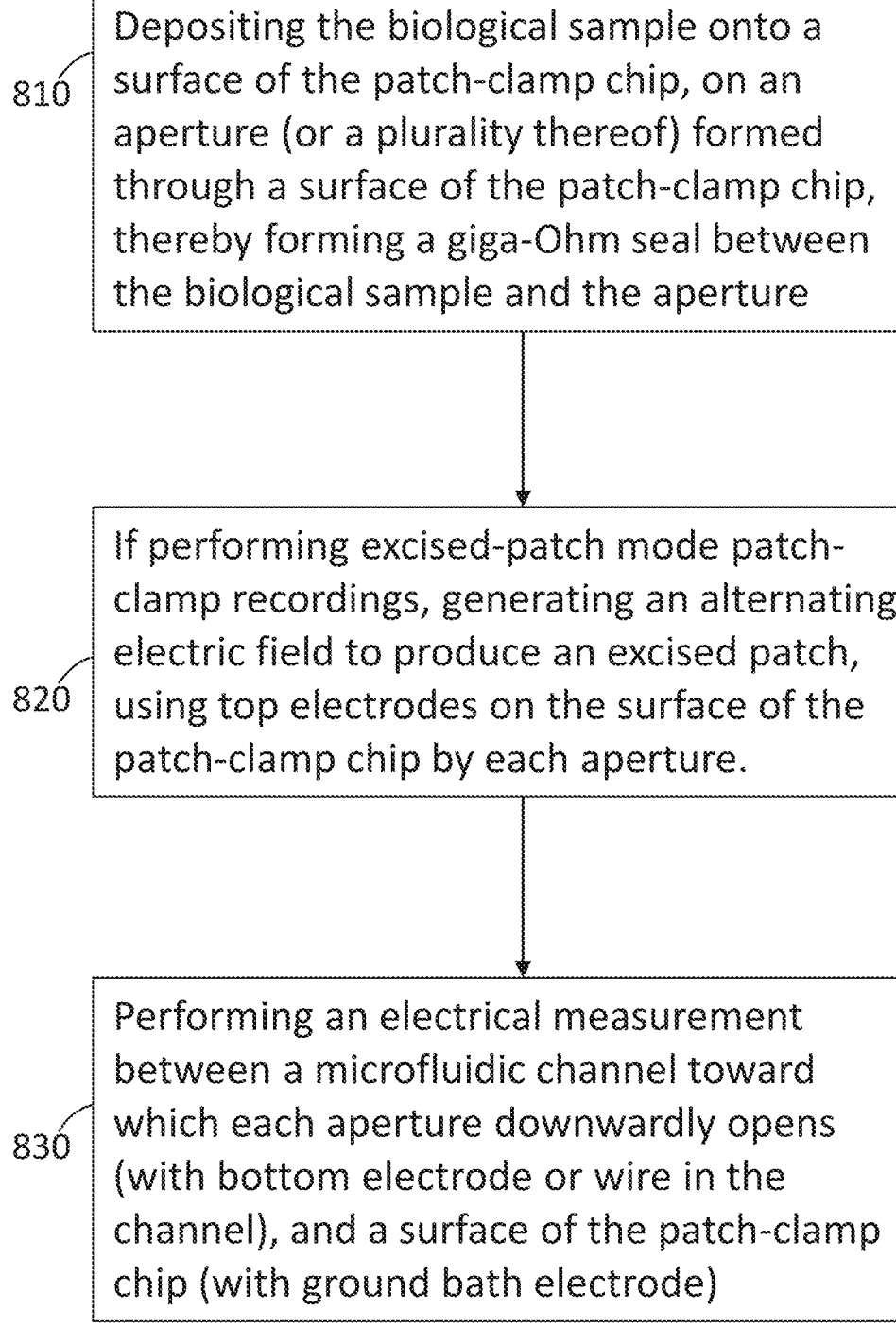
FIG. 8 is a flowchart illustrating a method of performing electrophysiological measurements using a patch-clamp chip, according to an embodiment.

The resulting device can form a patch-clamp chip, as described above, for performing electrophysiological measurements. FIG. 8 is a flowchart illustrating a method for performing electrophysiological measurements on a biological sample using a patch-clamp chip, the method comprising:

Step 810: depositing the biological sample onto a surface of the patch-clamp chip, on an aperture (or a plurality thereof) formed through a surface of the patch-clamp chip, thereby forming a giga-Ohm seal between the biological sample and the aperture; and Step 820: If performing excised-patch mode patch-clamp recordings, generating an alternating electric field to produce an excised patch, using top electrodes on the surface of the patch-clamp chip by each aperture.

Step 830: performing an electrical measurement between a microfluidic channel toward which each aperture downwardly opens (with bottom electrode or wire in the channel), and a surface of the patch-clamp chip (with ground bath electrode).

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method of fabrication of a multilayer PDMS object comprising poly-dimethylsiloxane (PDMS), the method comprising:

forming a current layer of PDMS on a previous layer of PDMS, or on a substrate if the current layer of PDMS is a first layer;

curing the current layer of PDMS along with the previous layer of PDMS, or with the substrate if the current layer of PDMS is the first layer;

applying a photolithography mask and a radiation in the deep UV range on the current layer of PDMS to create a pattern exposed to the radiation on the current layer of PDMS;

repeating the steps of forming, curing and applying to another current layer of PDMS distinct from the first layer, wherein said repeating is performed for a plurality of said other current layer of PDMS thereby building a stack of a plurality of PDMS layers, so that the pattern of the other current layer of PDMS is interconnected with the pattern of said previous layer of PDMS; and dissolving the pattern created in each layer of PDMS of the stack of PDMS layers by placing the stack of PDMS layers in a solution to form a microfluidic channel extending across more than one of said each layer where said pattern of the other current layer of PDMS was interconnected with the pattern of the previous layer of PDMS prior to said dissolving.

2. The method of claim 1, wherein applying the photolithography mask comprises locating the photolithography mask over the current layer of PDMS to create microfluidic channels in the pattern of the current layer of PDMS.

3. The method of claim 1, wherein the solution comprises a 1:1 mixture of: NaOH in water, and an alcohol chosen among: propanol, ethanol or methanol.

4. A patch-clamp chip comprising the multilayer PDMS object fabricated using the method of claim 1.

5. The method of claim 1 wherein each layer of PDMS of the stack of PDMS layers has a thickness ranging from 5 to 10 μm (0.2 to 0.4 mil).

* * * * *